United States Patent [19]
Gonser

[11] Patent Number: 5,203,696
[45] Date of Patent: Apr. 20, 1993

[54] FIBER-OPTIC PROTECTANT FOR HEAT STERILIZABLE INSTRUMENTS

[75] Inventor: Donald I. Gonser, Lancaster, Pa.
[73] Assignee: Den-Tal-Ez, Inc., Valley Forge, Pa.
[21] Appl. No.: 737,176
[22] Filed: Jul. 29, 1991
[51] Int. Cl.$^5$ ............................ A61C 1/00; A61C 3/00
[52] U.S. Cl. ....................................................... 433/29
[58] Field of Search .................... 433/29; 128/633, 634, 128/4, 6; 385/12

[56] References Cited

U.S. PATENT DOCUMENTS

| | | | |
|---|---|---|---|
| 2,433,928 | 1/1948 | Sheldon | 49/77 |
| 3,051,035 | 5/1960 | Root | 88/1 |
| 3,817,595 | 6/1974 | Edelman et al. | 385/115 |
| 3,859,131 | 1/1975 | Miles | 117/33.3 |
| 4,341,205 | 7/1982 | Hosono et al. | 128/6 |
| 4,448,547 | 5/1984 | Wickersheim | 128/736 X |
| 4,703,997 | 11/1987 | Ijiri et al. | 350/96.23 |
| 4,784,144 | 11/1988 | Ono et al. | 128/6 X |
| 4,925,268 | 5/1990 | Iyer et al. | 385/12 |
| 5,000,901 | 3/1991 | Iyer et al. | 385/12 X |
| 5,047,627 | 9/1991 | Yim | 128/634 X |
| 5,057,277 | 10/1991 | Mauze et al. | 128/634 X |

OTHER PUBLICATIONS

Information About Silicone Fluids, Dow Corning 200 Fluid 0.065-1.0 cSt, Dow Corning Corporation, 1982.
Information About Silicone Fluids, Dow Corning 200 Fluid 1.5-5.0 cS, Dow Corning Corporation, 1982.
Information About Silicone Fluids, Dow Corning 510 Fluid Dow Corning Corporation, 1976.

*Primary Examiner*—Gene Mancene
*Assistant Examiner*—Nicholas D. Lucchesi
*Attorney, Agent, or Firm*—Howson & Howson

[57] ABSTRACT

The light transmissibility of a fiber-optic bundle such as contained in a medical/dental instrument is maintained by the application to the polished and ground end surfaces of the bundle of a thin, substantially-transparent, heat-resistant, hydrophobic compound such as a silicone oil or grease.

18 Claims, 2 Drawing Sheets

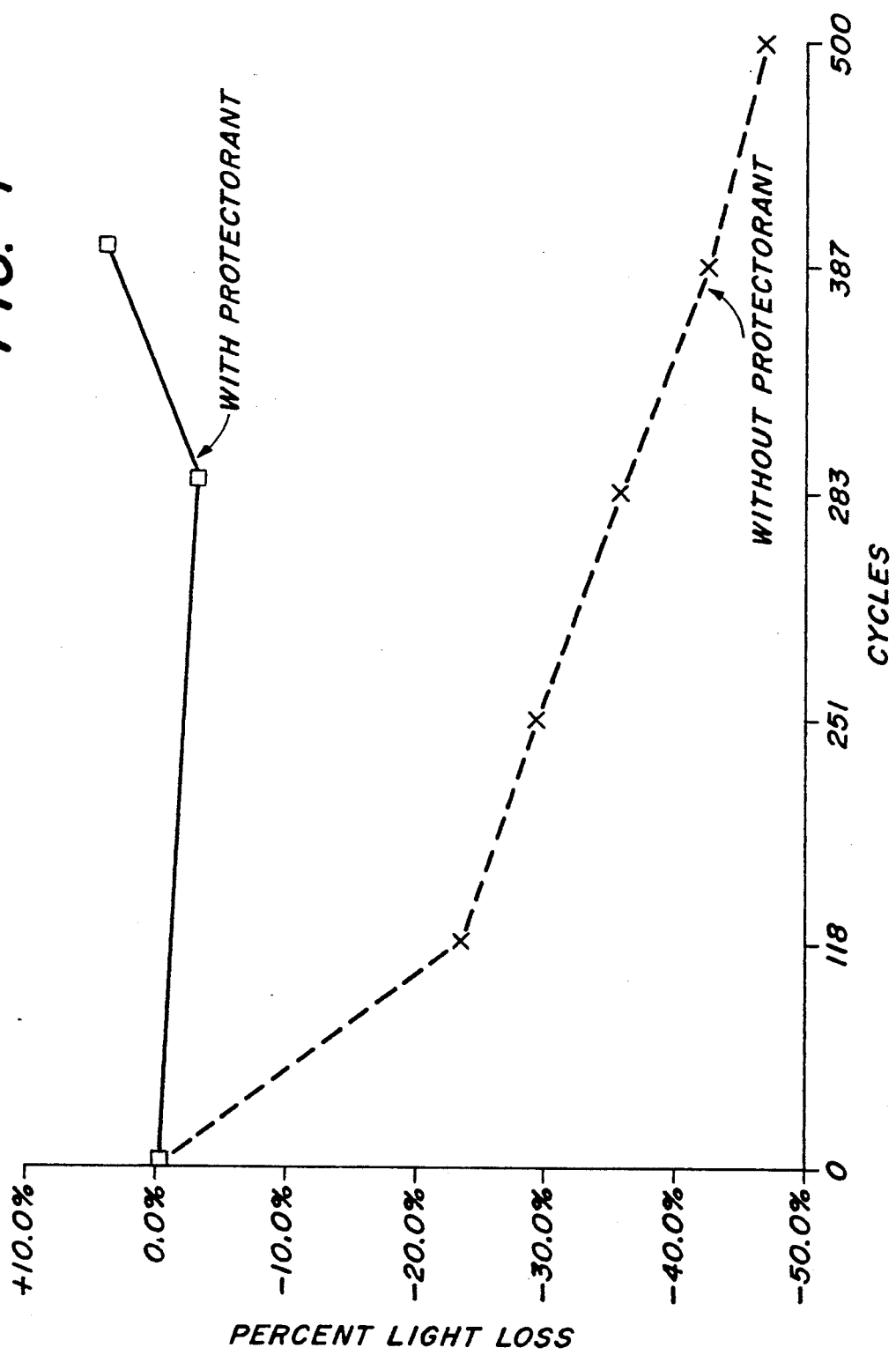

FIBER-OPTIC PROTECTANT FOR HEAT STERILIZABLE INSTRUMENTS

FIELD OF THE INVENTION

The present invention relates to fiber-optic medical and dental instruments, and more particularly, the present invention relates to instruments such as fiber-optic dental handpieces and endoscopes which are periodically heat sterilized.

BACKGROUND OF THE INVENTION

In the modern dental operatory, handpieces are provided with spot sources of illumination which enable a dentist to observe and operate upon teeth and related structures. A typical handpiece projects one or more light beams laterally from the proximal end of a handle onto a drill, or burr. Light is emitted from a lamp either located in the handle or through fiber optics from a remote light source and transmitted through the handpiece via means of an optical light path that includes a fiber-optic assembly permanently mounted in a handpiece. A particularly desirable handpiece is capable of projecting color-corrected light and is disclosed in U.S. Pat. No. 5,003,434 issued to the assignee of the present application. It is sold under the registered trademark COLORight ®.

Most dental handpieces are connected to a delivery system by a tubing which supplies air, water and electricity to a swivel connection. The swivel connection contains a lamp housing assembly adapted to be connected to a dental handpiece which also contains fiber-optics. The tubing and swivel also provide the air and water supply to the handpiece. The swivel enables the handpiece to be readily connected to, and disconnected from, the delivery system for cleaning and sterilization by conventional procedures.

There are several conventional heat sterilization procedures. One procedure involves a so-called chemiclave in which the handpiece is subjected to biocidal chemicals in a hot pressurized environment. The vapor phase of alcohol is used, and a percentage of water (12–15 percent) is always present. In an autoclave the sterilization procedure utilizes water, heat and pressure. The autoclave generates 100% water vapor to which the handpiece is subjected. For instance, in an autoclave, temperatures are developed in a range of 240°–275° F. where super-atmospheric pressures are present. The combination of heat, pressure and moisture (water) causes the degradation of fiber-optic assemblies located in the handpiece.

A major problem with respect to handpiece life is the degradation in the output of light after a fiber-optic handpiece has been subjected to repeated autoclave sterilization cycles. On average, in the chemiclave, fiber-optic handpieces experience an approximately 10% to 20% reduction in light output from as-manufactured conditions after 1200 chemiclave sterilization cycles. In an autoclave, in contrast, there is an approximate 70 percent reduction in light output after 1200 sterilization cycles. Thus, it should be apparent that at least with respect to autoclave sterilized handpieces, the dentist perceives very early in the expected life of the handpiece a decrease in the intensity of light output, and this is obviously very undesirable. The cost to replace some high quality handpiece fiberoptics can be as high as $300, whereas the original cost of this same handpiece may be $600.00.

When one considers that a handpiece should be capable of withstanding over 2000 sterilization cycles with minimal maintenance, a fiber-optic replacement of $300 is far too high in cost to be commercially acceptable. In the case of some endoscopes, coherent viewing fiber-optic assemblies suffer from the same problem and may cost up to $2000 to replace. It should be apparent that there is a real need for a fiber-optic handpiece capable of projecting light over a 2000 autoclave cycle time period and to be able to deliver substantially undiminished light intensity with minimal maintenance.

OBJECTS OF THE INVENTION

With the foregoing in mind, a primary object of the present invention is to provide a novel method for maintaining the light output from a fiber-optic medical or dental instrument at substantially its as-manufactured light intensity for a prolonged period of time despite subjecting the handpiece to repeated heat sterilization cycles.

Another object of the present invention is to provide an improved means for protecting ground and polished end surfaces of a fiber-optic light carrier or cable to prevent damage due to repeated exposure to elevated temperatures, in combination with the presence of moisture.

A further object of the present invention is to provide an inexpensive and easy way to apply protectant coating for ground and polished end surfaces of a fiber-optic cable to reduce the degradation in light intensity due to repeated exposure to a hostile environment posed by super-atmospheric pressure, heat and moisture.

Another object is to prevent degradation of fiber-optics having fiber ends (input and output of light) arranged in a coherent pattern used by the operator to view an object, such as, through an endoscope commonly used in the medical/surgical field by using the same protective process as with a light delivery fiber-optic system.

As yet another object, the present invention provides a novel technique for extending the efficient utilization of a fiber-optic cable that is exposed repeatedly to hostile sterilization environments such as encountered in a chemiclave, an autoclave and to a lesser extent a dryclave.

SUMMARY OF THE INVENTION

More specifically, the present invention provides an improvement in medical, or dental, handpieces and instruments having a glass fiber-optic cable for transmitting light between light into and out of fiber end surfaces which are optically ground and polished and wherein the handpiece or instrument is subjected to periodic sterilization cycles involving heat and moisture. The improvement comprises a thin coating of a transparent, or substantially transparent, heat-resistant hydrophobic compound applied to light input and output end surfaces. The coating provides a protectorant to the fiber ends to prevent water absorption into the fiber ends and their epoxy fiber binder when subjected to repeated heat sterilization cycles where water (moisture) is present. Thus, a maximum of protection is provided resulting in a minimum degradation over time in the light input and output surfaces of the fibers. Preferably, the compound is chemically stable at temperatures up to at least 400° F., and it may include a silicone dispersed in a fluid carrier. The compound is applied by a method which involves coating the end surfaces, preferably periodically and after being cleaned.

BRIEF DESCRIPTION OF THE DRAWINGS

The foregoing and other objects, features and advantages of the present invention should become apparent from the following description, when taken in conjunction with the accompanying drawings, in which;

FIG. 4 is a graph illustrating the change in light transmission for an averrage of several handpieces, the data being presented as a percent of light loss vs number of autoclave cycles where fiber-optic handpieces have been subjected to periodic heat with water (moisture) as used in an autoclave sterilization cycle.

DESCRIPTION OF THE PREFERRED EMBODIMENT

Figure 1:
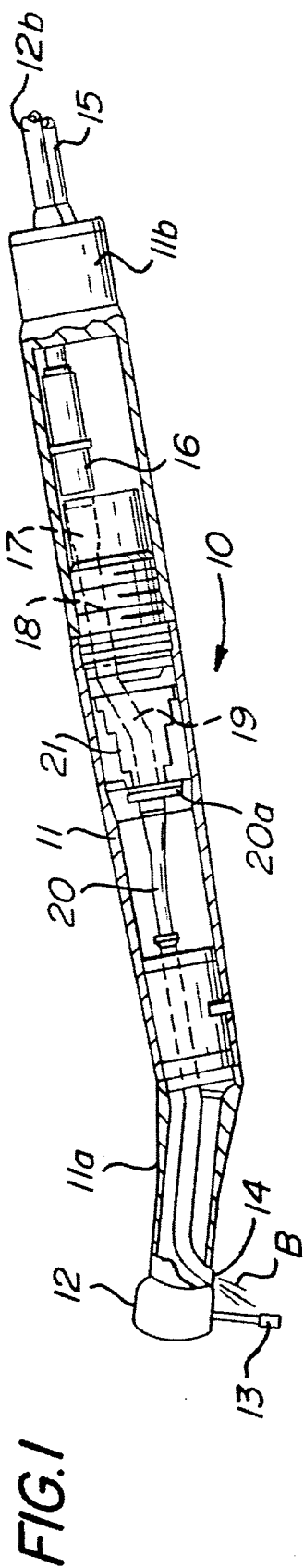
FIG. 1 is a side elevational view of a dental handpiece embodying the present invention, portions of the handpiece having been broken away and sectioned to illustrate certain interior details of construction.

Referring now to the drawings, FIG. 1 illustrates a hand-held instrument 10 for use in providing spot illumination of a work location. In the present instance, the instrument 10 is a dental handpiece which includes an elongated handle portion 11 having a proximal end portion 11a mounting an air turbine 12 for rotating either a drill, or a burr, 13 adapted to operate on a tooth or other structure in a conventional manner. The air supply and exhaust for the turbine 12 are provided by flexible elongated tubes, such as the tube 12b connected to the distal end 11b of the handle 11 and routed internally through the handle 11 in a conventional manner.

For purposes of illuminating the drill 13 and tooth it is known to provide the handpiece 10 with means for projecting a light beam in the region of the drill 13. To this end, the light beam projecting means includes at least one, and preferably a pair of light emission or exit ports 14 mounted in the proximal end portion 11a of the handle 11 and canted in the direction of the drill 13 to project light laterally in the manner illustrated in FIG. 1. In the illustrated embodiment, the light is provided by an electrically-powered lamp carried in the handle 11 and supplied with electricity by a power cable 15 associated with the air supply, water supply and air exhaust tubing.

Preferably, the electrically-powered source of illumination includes a tungsten-halogen lamp 16 mounted adjacent to the distal end portion 11b of the handle 11 and disposed with its lamp light output lens facing toward the proximal end 11a of the handle 11. Light from the lamp 16 is transmitted lengthwise of the handle 11 via an optical path provided by a series of endwise disposed optically-transparent elements, including a clad rod optical coupling 17, an optical transmission fused rod element 18 which continues through the region 19 to the end of the handpiece swivel where the handpiece fiber-optic bundle interfaces with the fused rod. The bifracted optical bundles 20 terminate in the light ports 14 at the proximal end portion 11a of the handpiece 10. Thus, light generated by the lamp 16 is transmitted lengthwise of the handle 1 and projected in optical beams B onto the drill or burr 13.

As described thus far, the construction of the dental handpiece 10 is conventional. Such construction is found in a handpiece sold by the assignee of the present application under the Trademark STAR Model 430 SWL.

Figure 3:
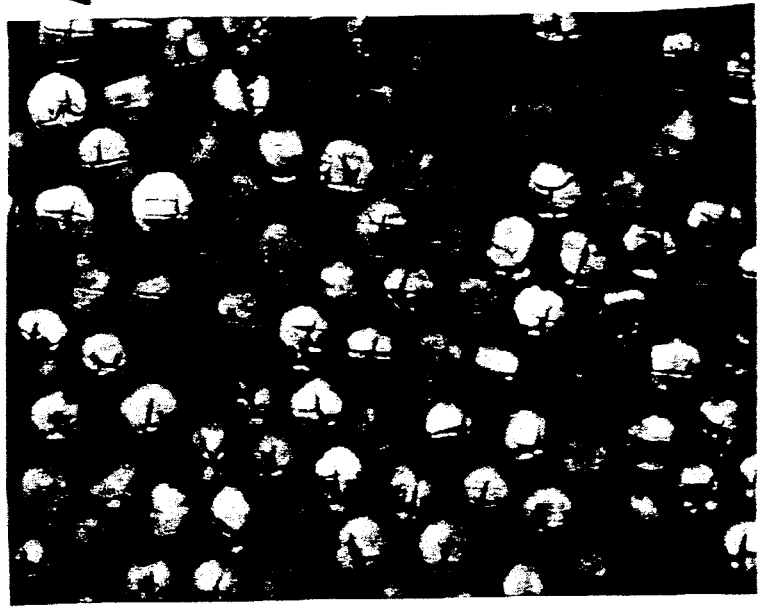
FIG. 3 is a photomicrograph similar to FIG. 2, but illustrating the condition of an end surface treated in accordance with the present invention tested under the same autoclave conditions.

As manufactured, the polished and ground end surface of the light port 14, when greatly magnified, appears as shown in FIG. 3. As illustrated, the end surfaces of each of the glass fibers in the fiber bundle 20 has a circular cross-section and the fibers are separated laterally along their length by an epoxy binder. The opposite end of the fiberoptic cable 20 terminates at the interface 20a of the fiber-optic bundle and fused rod 19 at the forward end of the female part of the swivel 21.

After repeated sterilization cycles in a hostile environment, such as an autoclave, wherein the handpiece is subjected to temperatures in the range of 240° F. to 275° F. in the presence of moisture and a super-atmospheric pressure on the order of 32 psi, the end surfaces of the glass fibers tend to absorb moisture. They then start to crack and finally separate. The epoxy binder also disintegrates in the region of the fiber ends also due to water absorption which is greatly accelerated by autoclaving. As a result, the end surfaces lose their lateral support, and this, combined with the water absorption into the glass alloy fiber results in chipping and erosion of the end fiber-optic surfaces. Both of these water absorption mechanisms interfere with the transfer of light at the light input and output areas of the fiber-optic bundle located at the ports 14 and light input end 20a.

Figure 2:
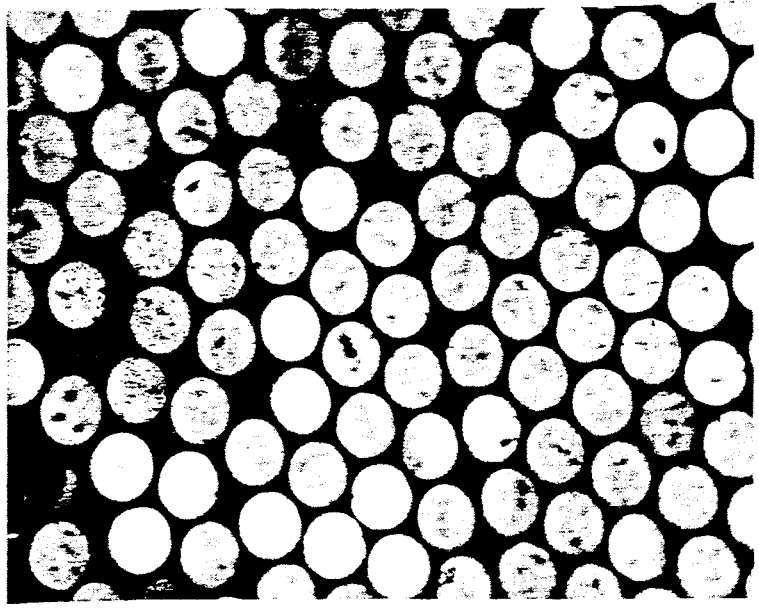
FIG. 2 is a photomicrograph of a ground and polished end surface of a fiber-optic bundle in a state-of-the-art handpiece after repeated heat sterilizations utilizing heat and water (moisture) in the hostile environment of an autoclave.

By way of example, the photomicrograph illustrated in FIG. 2 shows the condition of the ground and polished end surfaces of a fiber-optic bundle after 238 sterilization cycles in an autoclave. Sterilization cycles vary depending upon the equipment, but in a typical procedure, a handpiece is placed in an autoclave. The temperature and pressure of a typical autoclave is raised to 250° F. which raises the pressure to about 32 psi where the atmosphere is nearly 100% water vapor by weight. The handpiece is retained in the autoclave for 15 minutes (a typical schedule) after which time the pressure is returned to atmospheric, and the handpiece is typically allowed to cool before being removed from the autoclave. This procedure was repeated 238 times before the photomicrograph of FIG. 2 was taken.

A fiber-optic cable having the deteriorated structure illustrated in FIG. 2 transmits significantly less light than it transmitted in its as-manufactured condition. In order to prevent the condition illustrated in FIG. 2 from occurring, and to maintain the light transmission of a fiber-optic-cable, the present invention involves the application to a ground and polished end surface of a fiber-optic cable of a thin coating of a substantially transparent, heat-resistant hydrophobic compound. One preferred compound includes a silicone compound, such as a synthetic silicone oil or grease. A preferred compound must be chemically stable at temperatures up to at least 400° F. In other words, the compound must not break down chemically at temperatures encountered in a conventional sterilization procedure, including a dry-clave where temperatures reach 375° F. A preferred compound is SPRAYON manufactured by Sherwin Williams of Bedford Heights, Ohio 92806. A thin coating of the compound is preferably applied by means of a cotton swab. Preferably, the ground and polished end surfaces are cleaned by means of a solvent, such as isopropyl alcohol, before the substantially transparent, heat-resistant hydrophobic protectant compound is applied as described.

The protectant compound is applied to the fiber-optic surfaces when the handpiece is manufactured and before being shipped. Thereafter, the compound may be, and preferably is, applied at periodic intervals between 50 and 100 sterilization cycles. It has been found that this application regimen maintains the optical transmission of the fiber-optic cables at substantially their as-manufactured, un-coated, condition after almost 400 sterilization cycles. For example, the photomicrograph illustrated in FIG. 3 of a fiber-optic cable end surface treated in accordance with the present invention was taken after 397 sterilization cycles in an autoclave. As noted heretofore, the fiber-optic end surface of FIG. 2 is the result of only 238 sterilization cycles in an autoclave. A comparison of FIGS. 2 and 3 indicates the differences in physical condition of a handpiece fiber-optic cable end surface with and without treatment in accordance with the present invention.

One preferred compound includes a silicone. Silicone is most preferred because, it is believed, it does not combine with water and is a true hydrophobic composition which acts to prevent water absorption into the glass and epoxy binder. Fused rods do not include an epoxy binder, but nevertheless water absorption will attack and degrade the glass alloy and the protectorant would protect this type of optical construction also.

Although the precise theory by which the present invention functions cannot be fully explained, it is believed that the metals alloyed in the glass fibers chemically react with water at elevated temperatures and under pressure cause the deterioration process to be greatly accelerated, resulting in rapid deterioration as illustrated in FIG. 2. It has been found that a thin layer of the silicone applied in the manner disclosed provides a durable, hydrophobic, heat-resistant, transparent coating for the end surfaces of the glass fibers. Furthermore, the epoxy binder which binds the fibers together into a bundle receives the same protection. It is not currently known whether or not periodic re-coating is necessary in order to maintain the optical transmission of the fiber-optic bundle, but tests to date reveal that periodic coating is highly desirable because the schedule maintains light transmission to the as-manufactured level.

To demonstrate graphically the significance of the present invention to maintain the as-manufactured optical transmission, tests have been conducted on several fiber-optic handpieces which were identical except for the application. The average of several handpieces having the coating described and the non-application of anything to the others. The light transmission of the handpieces was measured periodically utilizing a calibrated standard lamp source and EG & G 880 spectroradiometer light measurement system which was calibrated and traceable to a National Bureau of Standards standard lamp. Repeat testing for comparative purposes yields a light testing accuracy which is repeatable within ±6% of an average value.

FIG. 4 illustrates the percentage loss in light transmission relative to sterilization cycles for several handpieces in each group of the tested handpieces. Although the average of several handpieces of the present invention indicates a slight increase in light transmission, it is concluded that the small increase in light transmission is due to limitations set forth by test accuracy limitation pertaining to repeat testing using the EG & G 880 light measurement system. Hence, the data should be considered as indicating no significant loss in light transmission after 387 sterilization cycles.

While the above-referenced SPRAYON Products silicone, or Dow Corning #4 silicone grease, has been found to function satisfactorily, other synthetic non-silicone high temperature greases and oils work effectively, such as Chevron SR-1 grease No. 2. Still other equivalent high temperature type compounds in the form of oils or greases, should function satisfactorily for the intended purpose. The coating may be applied either by direct application with a cotton swab as described, or by spraying the fiber-optic ends in an aerosol form, or it can be spatulated on the part using a flat wooden tongue depressor.

While applications of the coating to at least one end surface will provide some advantage, maximum advantage is realized by applying the coating to both opposite end surfaces of a fiber-optic cable bundle. Providing a moisture barrier to both fiber-optic ends prevents deterioration to light transmission. The thickness of the coating should be less than about 1.0 mil for a grease. A thin low viscosity fluid applied to the fiber-optic ends will appear to "soak" up into the ends. Coating thickness is far less than 1.0 mil using a low viscosity protectorant. The coating itself should have a visible light transmission between 380 nm and 760 nm greater than 95% when measured at a thickness of 1.0 mil. It is further contemplated that the low viscosity coating may be followed by an application of a high viscosity material grease. Other characteristics of the preferred coatings should also include the following:

(1) The material formulation must meet safety requirements for human toxicity where trace amounts of the protectorant may come in contact with mucous membranes; and (2) A combination of low viscosity material can be applied initially followed by high viscosity application to assure a greater level of protection from moisture penetration, which combination would enhance the method for maximum effectiveness.

From the foregoing, it should be apparent that the present invention provides a unique way to preserve the original optical transmission of a fiber-optic cable system subjected to repeated exposure of hostile environments characterized by heat, pressure and moisture. While the present invention has been described particularly with respect to a dental handpiece, it should be apparent that it has applicability to other instruments utilized in dental and medical applications, including endoscopes, laryngoscopes, laproscopes and the like which incorporate fiber-optics and which require periodic heat sterilization. Accordingly, while a preferred embodiment of the present invention has been described in detail, various modifications, alterations and changes may be made without departing from the spirit and scope of the present invention as defined in the appended claims.

I claim:

1. In a medical/dental instrument subjected to periodic sterilization cycles involving heat and moisture, the instrument having a glass fiber-optic assembly mounted therein for transmitting light into and from surfaces which are located at opposite ends of the assembly and which are optically ground and polished, the improvement comprising a thin coating of a substantially transparent, heat-resistant, hydrophobic compound applied on both of said surfaces, whereby the instrument can be subjected to repeated sterilization cycles with minimal degradation in the light transmission into and out of the fiber-optic assembly.

2. The improvement according to claim 1 wherein said compound is chemically stable at temperatures of at about 400° F.

3. The improvement according to claim 2 wherein said compound includes a silicone in a lubricant carrier.

4. The improvement according to claim 2 wherein said compound includes a silicone grease.

5. The improvement according to claim 2 wherein said compound includes a silicone oil.

6. The improvement according to claim 2 wherein said compound is chemically formulated to operate at temperatures of at least 400° F. without a chemical change and is in a fluid state when applied.

7. In a heat sterilizable medical/dental handpiece having a glass fiber-optic assembly with ground and polished end surfaces at opposite ends thereof, the improvement comprising a thin, substantially transparent, heat-resistant, hydrophobic, compound coating applied onto both of said end surfaces, said compound being characterized by shearability at room temperatures and chemical stability at temperatures up to at least about 400° F., whereby the handpiece can be subjected to at least fifty sterilization cycles in a hot and moist environment without significant degradation with respect to light input, transmission over its length, and light output from the fiber-optic assembly.

8. The improvement according to claim 7 where said compound is a high temperature synthetic compound.

9. The improvement according to claim 8 where said compound is a silicone compound.

10. In a heat sterilization process wherein a medical/dental handpiece having a glass fiber-optic cable with ground and polished end surfaces is subjected to repeated heat sterilizations in a hostile environment characterized by temperatures in excess of 200° F. and moisture under pressure, the improvement wherein a thin coating of a substantially transparent, heat resistant, hydrophobic compound is applied to both of said end surfaces at least once to preserve the light transmission of the cable by preventing degradation of the ground and polished end surfaces into which and from which visible light is projected, whereby the light transmission of the cable can be maintained at its substantially like-new level for a prolonged period of time.

11. The process of claim 10 wherein said hydrophobic compound is characterized by chemical stability to temperatures above 400° F.

12. The process of claim 10 wherein said compound is a synthetic silicone grease.

13. The process of claim 10 wherein said compound is a synthetic silicone oil.

14. The process of claim 10 wherein said compound is a synthetic oleoganeous formulation characterized as stable when subjected to temperatures greater than 400° F. temperature.

15. The process of claim 10 wherein said compound is applied periodically after about 50 autoclave, chemiclave or dry heat sterilization cycles.

16. The process according to claim 10 including the step of cleaning said surfaces before applying said compound.

17. The process of claim 10 including the step of applying said compound in two steps: one as a low viscosity material oil followed by the other as an application of a high viscosity material grease.

18. The improvement according to claim 7 wherein said compound includes a layer of low viscosity oil and a layer of high viscosity grease on said oil layer.

* * * * *